US008772240B2

(12) United States Patent
Matthiessen et al.

(10) Patent No.: US 8,772,240 B2
(45) Date of Patent: Jul. 8, 2014

(54) ETHANOL DEPENDENCE OF ALPHA1 ANTITRYPSIN C-TERMINAL LYS TRUNCATION BY BASIC CARBOXYPEPTIDASES

(75) Inventors: Peter Matthiessen, Vienna (AT); Alfred Weber, Vienna (AT); Peter Turecek, Klosterneuburg (AT); Hans-Peter Schwarz, Vienna (AT)

(73) Assignees: Baxter International Inc., Deerfield, IL (US); Baxter Healthcare SA, Glattpark (Opfikon)

( * ) Notice: Subject to any disclaimer, the term of this patent is extended or adjusted under 35 U.S.C. 154(b) by 1689 days.

(21) Appl. No.: 11/749,944

(22) Filed: May 17, 2007

(65) Prior Publication Data
US 2007/0274976 A1 Nov. 29, 2007

Related U.S. Application Data

(60) Provisional application No. 60/801,644, filed on May 19, 2006.

(51) Int. Cl.
*A61K 38/57* (2006.01)
*C07K 14/81* (2006.01)

(52) U.S. Cl.
CPC .............. *A61K 38/57* (2013.01); *C07K 14/8125* (2013.01)
USPC ......... 514/15.3; 514/20.3; 424/94.2; 435/184

(58) Field of Classification Search
CPC .......................... A61K 38/57; C07K 14/8125
USPC ................. 514/15.3, 20.3; 424/94.2; 435/184
See application file for complete search history.

(56) References Cited

U.S. PATENT DOCUMENTS 6,462,180 B1  10/2002  Lebing et al.

FOREIGN PATENT DOCUMENTS

WO  WO 98/00154 A1  1/1998
WO  WO 2004/060528 A1  7/2004

OTHER PUBLICATIONS

Definition of derivative and analog from http://cancerweb.ncl.ac.uk/omd/about.html, pp. 1-5. Accessed Jul. 7, 2005.*
Chen, S.X. et al.; "Purification of $\alpha_1$ Proteinase Inhibitor from Human Plasma Fraction IV-1 by Ion Exchange Chromatography"; 1998; *Vox Sanguinis*; vol. 74; pp. 232-241.
Coan, M.H.; "Purification of Alpha-1-Proteinase Inhibitor"; Jun. 24, 1988; *The American Journal of Medicine*; vol. 84(suppl 6A); pp. 32-36.
Cowden, D.I. et al.; "A Pilot Study Comparing the Purity, Functionality and Isoform Composition of Alpha-1-Proteinase Inhibitor (Human) Products"; 2005; *Current Medical Research and Opinions*; vol. 21(6); pp. 877-883.
Glaser, C.B. et al.; "The Isolation of Alpha-1-Protease Inhibitor by a Unique Procedure Designed for Industrial Application"; 1982; *Analytical Biochemistry*; vol. 124; pp. 364-371.
International Search Report mailed on Sep. 17, 2007, for PCT Application No. PCT/EP2007/004428 filed on May 17, 2007, seven pages.
Jirgensons, B.; "Circular Dichroism Studies on the Effects of Ethanol on the Conformation of $\alpha_1$-Acid Glycoprotein, $\alpha_1$-Antitrypsin, Deoxyribonuclease, Pepsinogen, Soybean Trypsin Inhibitor and Unfolded Ribonucleases"; 1978; *Biochimica et Biophysics Acta*; vol. 534; pp. 123-131.
Kolarich, D. et al; "Biochemical, Molecular Characterization, and Glycoproteomic Analyses of $\alpha_1$ Proteinase Inhibitor Products Used for Replacement Therapy"; Nov. 2006; *Transfusion*; vol. 46; pp. 1959-1977.
Mattes, E. et al.; "Preparation and Properties of an Alpha-1-Protease Inhibitor Concentrate with High Specific Activity"; 2001; *Vox Sanguinis*; vol. 81; pp. 29-36.
Weber, A. et al.; "Convenient High-Resolution Isoelectric Focusing (IEF) Method for the Separation of Alpha$_1$ -Proteinase Inhibitor (A1PI) Isoforms in A1PI Concentrates"; 2007; *Journal of Pharmaceutical and Biomedical Analysis*; pp. 1-5.

\* cited by examiner

*Primary Examiner* — Julie Ha
(74) *Attorney, Agent, or Firm* — Morgan, Lewis & Bockius LLP

(57) ABSTRACT

Methods of preparing alpha-1-antiproteinase inhibitor and controlling the amount of des-lys alpha-1-antiproteinase inhibitor in the preparation, and compositions comprising the same, as well as methods of treatment using the same are provided.

11 Claims, 8 Drawing Sheets

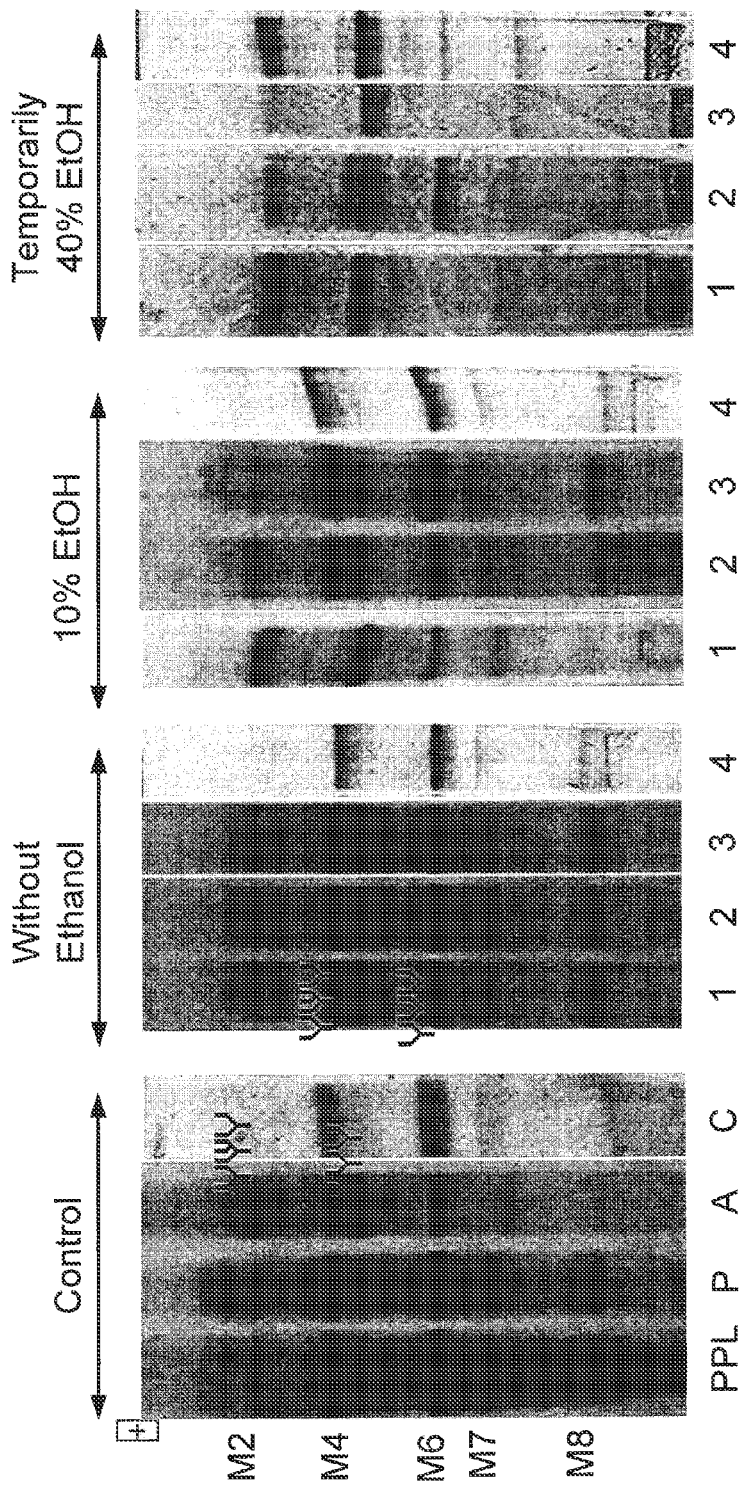

Concentration Dependent Cleavage with rCPM

A = Aralast; C = C-terminal intact A1PI before incubation with rCPM. Arrows indicate pI shift caused by C-terminal truncation (also affects minor bands M8 and M7).

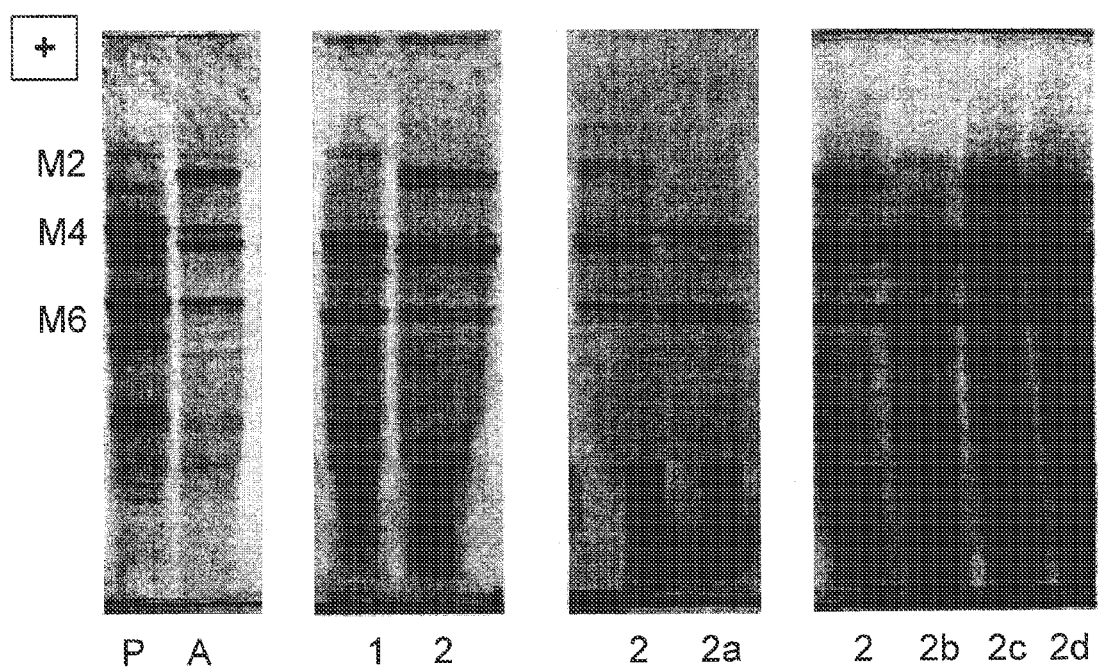

Fig. 3
Temporary Contact of Dissolved IV-1 Paste with
40% Ethanol and Inhibition of Cleavage by Inhibitors P = Prolastin; A = Aralast. IV-1 paste incubated with specific or non-specific inhibitor and after EtOH treatment. 1 = with 10% EtOH; 2 = 1h with 40% EtOH then dilution to 10%; 2a = +100 mM 6-aminocaproic acid; 2b, 2c, 2d = +10 µM, +100 nM, +1 nM respectively of CPN inhibitor 2-mercaptomethyl-3-guanidinoethylthiopropanoic acid.

Quantitative Measurement of Released Lys from A1PI by CPN: Effect of EtOH

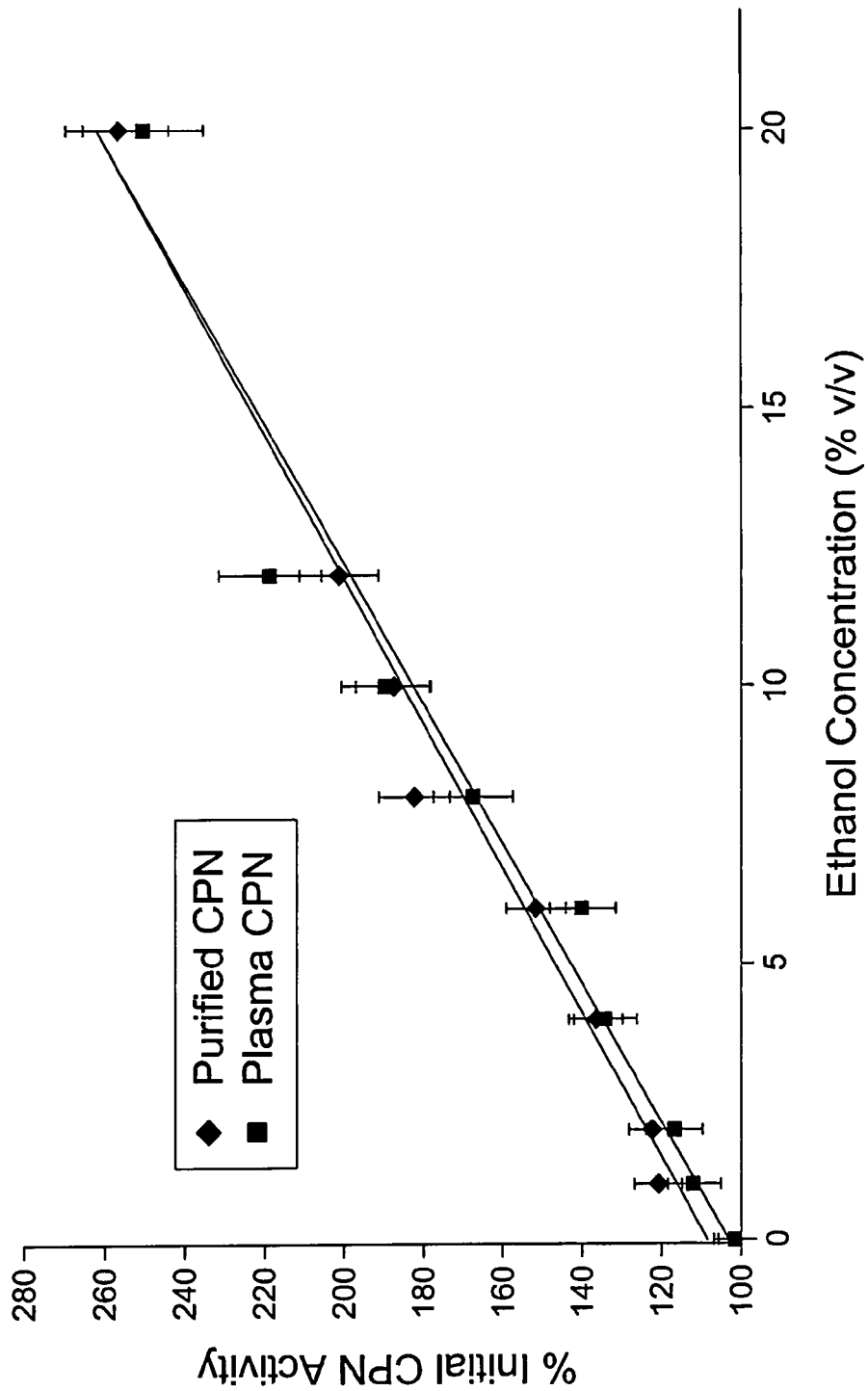

Detection of C-Terminal Truncated A1PI in a Human BAL Solution

P = Prolastin; A = Aralast; 1, 2, and 3 = human BAL samples.
3 (plasma) = plasma of BAL 3.

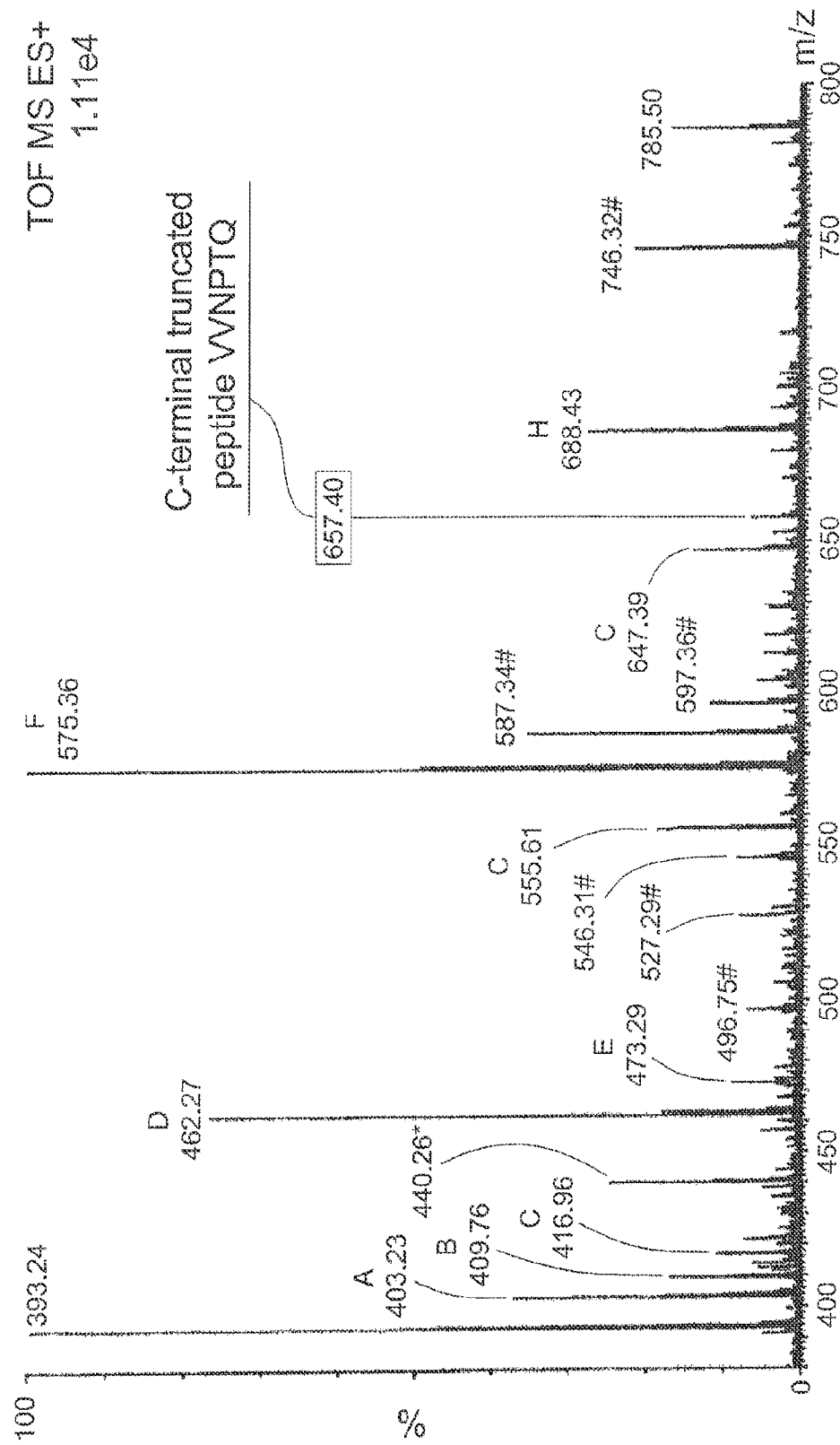

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic alpha1-proteinase inhibitor (A1PI)
      C-terminal truncated peptide

<400> SEQUENCE: 1

Val Val Asn Pro Thr Gln
 1               5
```

ETHANOL DEPENDENCE OF ALPHA1 ANTITRYPSIN C-TERMINAL LYS TRUNCATION BY BASIC CARBOXYPEPTIDASES

CROSS-REFERENCES TO RELATED APPLICATIONS

The present application claims priority to U.S. Ser. No. 60/801,644, filed May 19, 2006, herein incorporated by reference in its entirety.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

The invention relates to compositions of alpha1-proteinase inhibitor (A1PI) and methods of making and use.

Mature alpha1-proteinase inhibitor (A1PI) is a single chain glycoprotein composed of 349 amino acids and 12% carbohydrate (weight %) (see, e.g., Coan et al., Vox Sanguinis, 48:333-342 (1985)). Heterogeneity of A1PI is due to post-translational modifications and covalent linkage of 3 complex N-glycans to asparagines 46, 83 and 247[1,2]. The high negative charge of A1PI is the result of multiple sialic acid residues on N-glycans leading to multiple isoforms of A1PI (M1 to M8) that become visible after electrophoresis[3-8]. Two minor cathodal isoforms, M7 and M8, are the result of N-terminal truncation of 5 amino acids including negatively charged glutamic and aspartic acids[9].

A1PI belongs to the family of serpins that inhibit serine proteases. Neutrophil elastase, an enzyme which degrades a number of proteins of the interstitial extracellular matrix, is a serine protease that is inhibited by A1PI. In patients with inherited A1PI deficiency the balance between neutrophil elastase and A1PI is disturbed, which increases their risk of developing lung emphysema. In these patients, elastase released from neutrophils in the lower respiratory tract escapes neutralization by A1PI with consequent chronic destruction of lung parenchyma, which becomes clinically apparent in the third to fourth decade of life[10].

To slow down the progression of emphysema in patients with A1PI deficiency the protease—anti-protease balance is restored by life-long augmentation therapy with highly purified plasma-derived A1PI concentrates which raise A1PI in the circulation[11]. Three different products (Prolastin® (Alpha$_1$-Proteinase Inhibitor (Human)), Aralast® (Alpha$_1$-Proteinase Inhibitor (Human)) and Zemaira® (Alpha$_1$-Proteinase Inhibitor (Human))) are approved by the US FDA for the treatment of A1PI deficiency. These products are manufactured from large pools of ~10,000 liters of human plasma[12-14]. Upstream manufacturing and downstream purification processes including pathogen-reduction steps vary to differing extents between products[12,15,16]. After removal of the immune-globulin containing plasma fractions various sequential steps of the Cohn/ethanol fractionation, including chromatography, protein precipitation and co-precipitation followed by resolubilization, diafiltration for buffer exchange, concentration steps and viral reduction steps, take advantage of the physicochemical properties of A1PI to concentrate A1PI into an intermediate fraction. This fraction is used for subsequent downstream purification. A1PI is therefore exposed to different physicochemical conditions and to a variety of enzymes during the manufacturing process.

Available A1PI concentrates have a purity of >80% and specific activities ranging from 0.6 to 1.0 U A1PI/mg protein with different plasma protein impurity profiles. High resolution isoelectric focusing (IEF) analysis of A1PI present in A1PI products has revealed differences in the IEF band pattern of glycolsoforms and raised questions from patients, physicians and the FDA. This difference in electrophoretic mobility was not caused by differences in N-glycan profiles, but mainly by varying degrees of C-terminal lysine truncation at position 394 from the A1PI molecule adding an additional negative charge to the protein[8,17,18]. The percent of A1PI C-terminal truncation as compared to total A1PI protein differed in the three approved products. Aralast® (Alpha$_1$-Proteinase Inhibitor (Human)) showed approximately 60% (67%) truncated A1PI, while Prolast® (Alpha$_1$-Proteinase Inhibitor (Human)) showed 2% truncated A1PI and Zemaira® (Alpha$_1$-Proteinase Inhibitor (Human)) showed 6% truncated A1PI.

Basic carboxypeptidases are a group of enzymes that specifically cleave C-terminal basic amino acids (arginine or lysine) from peptides and proteins leading to an increased negative charge of the protein[19]. Basic carboxypeptidases are involved in a variety of biological processes such as food digestion, inactivation of complement components[20], inhibition of fibrinolysis[21] and processing of peptide hormones[22].

In this application, we show that A1PI belongs to the group of proteins that are a substrate for basic carboxypeptidases and that the C-terminal truncated form of A1PI also occurs naturally. We also describe the manufacturing conditions which result in the removal of the positively charged C-terminal lysine of A1PI by carboxypeptidases.

SUMMARY OF THE INVENTION

Thus, it is an object of the present invention to provide A1PI compositions with altered amounts of C-terminal lysine cleavage, methods of making the same, and methods of treatment using the same.

The present invention provides, in one aspect, a method of controlling the amount of des-lys alpha-1-proteinase inhibitor in an alpha-1-proteinase inhibitor composition derived from human plasma, the method comprising the step of altering the concentration of ethanol for Cohn fractions IV-1+IV-4. In one embodiment, the amount of des-lys alpha-1-proteinase inhibitor is lowered or raised.

In another embodiment, the amount of des-lys alpha-1-proteinase inhibitor is less that than about 65% but more than about 2% of total alpha-1-proteinase inhibitor in the composition. In another embodiment, the amount of des-lys alpha-1-proteinase inhibitor is less than about 65% but more than about 6%. In another embodiment, the amount of des-lys alpha-1-proteinase inhibitor is less than about 6% but more than about 2%.

In another embodiment, the amount of des-lys alpha-1-proteinase inhibitor is more than about 70% of total alpha-1-proteinase inhibitor in the composition. In another embodiment, the amount of des-lys alpha-1-proteinase inhibitor is more than about 75% of total alpha-1-proteinase inhibitor in the composition.

In another embodiment, the concentration of ethanol used to precipitate Cohn fractions IV or IV-1+IV-4 is about 50%. In another embodiment, the concentration of ethanol used to precipitate Cohn fractions IV or IV-1+IV-4 is about 40%. In another embodiment, the concentration of ethanol used to precipitate Cohn fractions IV or IV-1+IV-4 is less than 50% but more than 10%. In another embodiment, the concentration of ethanol used to precipitate Cohn fractions IV or IV-1+IV-4 is less than 50% but more than 30%. In another embodiment, the concentration of ethanol used to precipitate Cohn fractions IV or IV-1+IV-4 is less than 45% but more than 35%. In another embodiment, the concentration of ethanol used to precipitate Cohn fractions IV or IV-1+IV-4 is less than 40% but more than 15%. In another embodiment, the concentration of ethanol used to precipitate Cohn fractions IV or IV-1+IV-4 is less than 40% but more than 20%. In another embodiment, the concentration of ethanol used to precipitate Cohn fractions IV or IV-1+IV-4 is less than 40% but more than 25%. In another embodiment, the concentration of ethanol used to precipitate Cohn fractions IV or IV-1+IV-4 is less than 40% but more than 30%. In another embodiment, the concentration of ethanol used to precipitate Cohn fractions IV or IV-1+IV-4 is less than 40% but more than 35%.

In another embodiment, the concentration of ethanol used to precipitate Cohn fractions IV or IV-1+IV-4 is less than 40% but more than 10%. In another embodiment, the concentration of ethanol used to precipitate Cohn fractions IV or IV-1+IV-4 is less than 35% but more than 10%. In another embodiment, the concentration of ethanol used to precipitate Cohn fractions IV or IV-1+IV-4 is less than 30% but more than 10%. In another embodiment, the concentration of ethanol used to precipitate Cohn fractions IV or IV-1+IV-4 is less than 25% but more than 10%. In another embodiment, the concentration of ethanol used to precipitate Cohn fractions IV or IV-1+IV-4 is less than 20% but more than 10%. In another embodiment, the concentration of ethanol used to precipitate Cohn fractions IV or IV-1+IV-4 is less than 15% but more than 10%. In another embodiment, the concentration of ethanol used to precipitate Cohn fractions IV or IV-1+IV-4 is about 10%. In another embodiment, the pH of Cohn fractions IV-1 or IV-1+IV-4 is less than about pH 5.9. In another embodiment, the pH of Cohn fractions IV-1 or IV-1+IV-4 is more than about pH 5.9.

In another aspect, the present invention provides a method of increasing the amount of des-lys alpha-1-proteinase inhibitor in an alpha-1-proteinase inhibitor composition derived from human plasma, the method comprising the step of modulating the ethanol content of a precipitate comprising alpha-1-proteinase inhibitor, wherein the precipitate is selected from the group consisting of the Cohn IV-1 precipitate or the Cohn IV-1+IV-4 precipitate. In one embodiment, the ethanol content of the precipitate is less than 50% but greater than 10%. In another embodiment, the ethanol content of the precipitate is less than 50% but greater than 30%. In another embodiment, the ethanol content of the precipitate is less than 45% but greater than 35%. In another embodiment, the ethanol content of the precipitate is about 40%. In another embodiment, an amount of carboxypeptidase suitable to cleave the C-terminal lysine of alpha-1-proteinase inhibitor is added to the precipitate. In another embodiment, the carboxypeptidase is selected from the group consisting of carboxypeptidase N, carboxypeptidase U, carboxypeptidase M, or carboxypeptidase B.

In another aspect, the present invention provides a method of decreasing the amount of des-lys alpha-1-proteinase inhibitor in an alpha-1-proteinase inhibitor composition derived from human plasma, the method comprising the step of modulating the ethanol content of a precipitate comprising alpha-1-proteinase inhibitor, wherein the precipitate is selected from the group consisting of the Cohn IV-1 precipitate or the Cohn IV-1+IV-4 precipitate, and wherein the ethanol content of the precipitate is below 10%.

In another aspect, the present invention provides a method of increasing the amount of des-lys alpha-1-proteinase inhibitor in an alpha-1-proteinase inhibitor composition, the method comprising the step of adding to the composition an amount of carboxypeptidase suitable to cleave the C-terminal lysine of alpha-1-proteinase inhibitor. In one embodiment, the composition is derived from human plasma and is a precipitate selected from the group consisting of the Cohn IV-1 precipitate or the Cohn IV-1+IV-4 precipitate. In another embodiment, the carboxypeptidase is selected from the group consisting of carboxypeptidase N, carboxypeptidase U, carboxypeptidase M, or carboxypeptidase B. In another embodiment, the method further comprises the step of modulating the ethanol content of the composition, wherein the ethanol content is more than 10%. In another embodiment, the ethanol content is more than 10% but less than 50%. In another embodiment, the ethanol content is more than 10% but less than 40%. In another embodiment, the ethanol content is more than 30% but less than 50%. In another embodiment, the ethanol content is more than 35% but less than 45%. In another embodiment, the ethanol content is 40%.

In another aspect, the invention provides an alpha-1-proteinase inhibitor composition comprising a physiologically acceptable carrier and an amount of des-lys alpha-1-proteinase inhibitor that is less than about 65% but more than about 2% of total alpha-1-proteinase inhibitor in the composition. In another embodiment, the amount of des-lys alpha-1-proteinase inhibitor is less than about 65% but more than about 6%. In another embodiment, the amount of des-lys alpha-1-proteinase inhibitor is less than about 6% but more than about 2%. In another aspect, the invention provides an alpha-1-proteinase inhibitor composition comprising a physiologically acceptable carrier and an amount of des-lys alpha-1-proteinase inhibitor that is more than about 70-75% of total alpha-1-proteinase inhibitor in the composition.

In another aspect, the invention provides a method of treating familial emphysema, the method comprising administering a therapeutically effective amount of a composition comprising a physiologically acceptable carrier and an amount of des-lys alpha-1-proteinase inhibitor that is less than about 65% but more than about 2% of total alpha-1-proteinase inhibitor in the composition. In another embodiment, the amount of des-lys alpha-1-proteinase inhibitor is less than about 65% but more than about 6%. In another embodiment, the amount of des-lys alpha-1-proteinase inhibitor is less than about 6% but more than about 2%. In another aspect, the invention provides a method of treating familial emphysema, the method comprising administering a therapeutically effective amount of a composition comprising a physiologically acceptable carrier and an amount of des-lys alpha-1-proteinase inhibitor that is more than about 70-75% of total alpha-1-proteinase inhibitor in the composition.

BRIEF DESCRIPTION OF THE DRAWINGS

The invention will now be explained in more detail by way of the following Examples and drawing figures, to which, however, it shall not be restricted.

FIG. 1: Effect of different CPs on the IEF pattern of A1PI: PPL: normal plasma pool, P: Prolastin® (Alpha$_1$-Proteinase Inhibitor (Human)), A: Aralast® (Alpha$_1$-Proteinase Inhibitor (Human)): C: non-truncated A1PI. 1, CPB (1.3 U/ml), 2, CPN (2.7 U/ml), 3, CPU (1 U/ml), 4, rCPM (0.25 U/ml). Anode is on the top. The non-truncated A1PI preparation was incubated at 10 μM with different CPs without and with ethanol as indicated. Samples were loaded at 10 μM A1PI. The N-glycan structures of M6 and M4 and of the C-terminal truncated M6 and M4 in Aralast® (Alpha$_1$-Proteinase Inhibitor (Human)) are symbolized by bi- and tri-antennary structures.

FIG. 3: Effect of CP inhibitors on C-terminal lysine truncation of dissolved IV-1 paste that had been in temporary contact with 40% ethanol. P, Prolastin® (Alpha$_1$-Proteinase Inhibitor (Human)). A, Aralast® (Alpha$_1$-Proteinase Inhibitor (Human)). Anode is on the top. Ethanol treated IV-1 paste was dissolved in buffer (pH 8.8) and incubated during 6 h at 22° C. in the presence of two distinct CP inhibitors. 1: in the presence of 10% EtOH; 2:1 h in the presence 40% EtOH, then dilution to 10%; 2a: +100 mM 6-Amino caproic acid; 2b, 2c, 2d: +10 μM, +100 nM, +1 nM of a more specific CPN inhibitor 2-Mercaptomethyl-3-guanidinoethylthiopropanoic acid, respectively.

FIG. 5: Effect of ethanol on the activity of CPN. The activity of purified CPN (diamonds) or plasma (full squares) was measured at increasing ethanol concentrations and given as a percent of the initial activity. Activity was measured using Hip-Arg as substrate and the released hippuric acid was quantified by RP-HPLC relative to an o-methyl hippuric acid standard.

FIGS. 6A and 6B show detection of C-terminal truncated A1PI in a human BAL solution. (a) Immunoblots after IEF of BAL solutions: P, Prolastin® (Alpha$_1$-Proteinase Inhibitor (Human), A, Aralast® (Alpha$_1$-Proteinase Inhibitor (Human); 1, 2 and 3, human BAL samples. The IEF pattern of the corresponding plasma of BAL 3 is also shown. (B) MS spectrum with C-terminal peptides of A1PI. The peptide with m/z 657.40 representing the C-terminal truncated peptide VVNPTQ (SEQ ID NO:1) is highlighted.

DETAILED DESCRIPTION OF THE INVENTION

I. Introduction

Figure 2A:
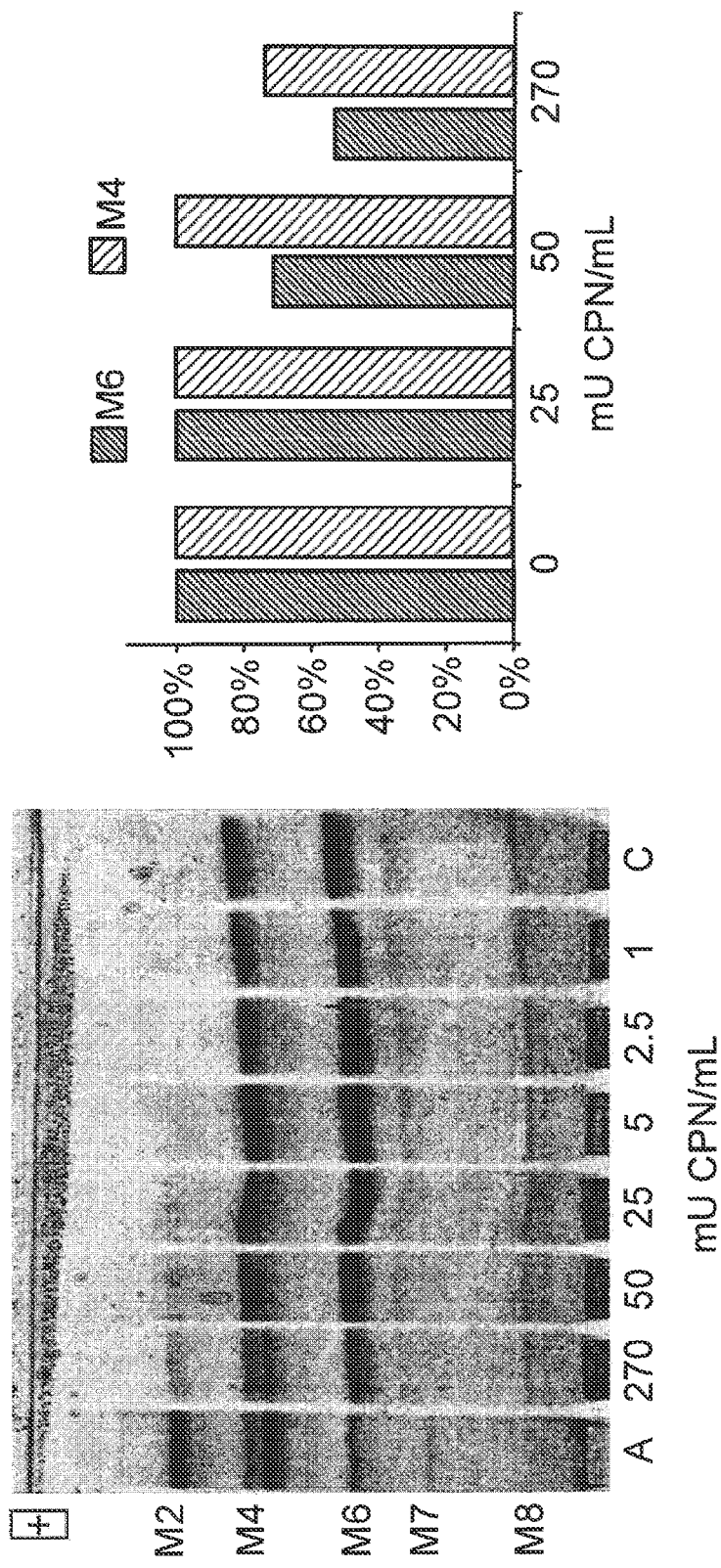
FIGS. 2A and 2B show A1PI cleavage at varying CPN and rCPM concentrations. A: Aralast® (Alpha$_1$-Proteinase Inhibitor (Human)), and C: non-truncated A1PI controls that were not treated with carboxypeptidase. The non-truncated A1PI (10 μM) was incubated after temporary exposure to 40% EtOH with (A) CPN (1-270 mU/ml) or (B) rCPM (1-250 mU/ml). Anode is on the top. The bar chart shows the results of the densitometric evaluation of the gel. The relative amount of non-cleaved bands M6 and M4 is shown as a percent of the sum of non-cleaved and C-terminal cleaved M6 and M4, respectively. Arrows in FIG. 2b indicate the pI shift caused by the C-terminal truncation affecting also the minor bands M8 and M7.

Patients with hereditary emphysema are treated with alpha1-proteinase inhibitor (A1PI) concentrates (also known as alpha1-antitrypsin). A deficiency in A1PI represents one of the most common lethal hereditary disorders of Caucasians in the United States and Europe. High resolution isoelectric focusing (IEF) analysis of A1PI show commercial products and plasma have different glycolsoform band patterns. The banding patterns reflect an anodic shift of glycolsoforms resulting from carboxypeptidases cleaving off the positively charged C-terminal lysine residue of A1PI. We showed that contact with ethanol during manufacture renders A1PI susceptible to the cleaving with the extent of Lys truncation depending on the ethanol concentration. Furthermore in contrast to cell-free systems, A1PI in broncho-alveolar lavage fluid is also partly Lys truncated. This is probably due to the presence of lipid-anchored carboxypeptidase M in lung tissue. Lys truncation in A1PI is therefore not only associated with manufacturing processes but is also a physiologic process.

Thus, modulation of the amount of the des-Lys form of A1PI is possible. Without being limited by theory, in one embodiment, lower amounts of the des-Lys form are desirable, for example, to improve serum stability and half life. In one embodiment, higher amounts of the des-Lys form are desirable, for example, in the case where the A1PI is administered by inhaling. A1PI in serum typically contains the C-terminal lysine, while the form present in the lung has a greater proportion of the des-Lys form.

II. Definitions

"Cohn fractionation" refers to the Cohn-Oncley fractionation procedure for human plasma. See, e.g., E. J. Cohn, et al., *J. Amer. Chem. Soc.*, 68, 459 (1946); E. J. Cohn, U.S. Pat. No. 2,390,074; and Oncley, et al., *J. Amer. Chem. Soc.*, 71, 541 (1949) the entire disclosures of which are hereby incorporated by reference herein. See also U.S. Pat. No. 6,284,874. The Cohn-Oncley process involves a series of cold ethanol precipitation steps during which specific proteins are separated according to isoelectric point by adjusting pH, ionic strength, protein concentration, temperature and ethanol concentration. See also U.S. Pat. No. 6,284,874

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). The dose can be administered parenterally, e.g., intravenously, or by inhalation.

"Hereditary emphysema" or "familial emphysema" refers to a genetic lung disease caused by A1PI deficiency. A1PI deficiency is also related to asthma, chronic obstructive pulmonary disease (COPD), chronic bronchitis, and broncheictasis. Patients with familial emphysema may be diagnosed or misdiagnosed with these disorders. Treatment of these disorders with A1PI is also contemplated by the present invention.

III. Methods of Making A1PI

A1PI is purified from an impure protein fraction. The impure protein fraction may be plasma, A1PI produced by recombinant methods or any other source comprising A1PI protein. In one embodiment A1PI is prepared from frozen plasma. The plasma is thawed and the Cohn IV-1 precipitate or the Cohn IV-1+IV-4 precipitate is prepared. The preparation of the Cohn IV-1 and the Cohn IV-1+IV-4 fraction are well known in the art and is described in U.S. Pat. No. 6,284, 874 (herein incorporated by reference), with modifications as described herein to modulate the amount of des-lys A1PI in the final preparation. Other methods of making A1PI are described, e.g., in U.S. Pat. No. 6,974,792. A1PI has also been produced recombinantly (see, e.g., Courtney, M. et al, *High-Level Production of Biologically Active Human Alpha*-1-*Antitrypsin in Escherichia coli*, Proc. Natl. Acad. Sci. USA 81: 669-673 (1984)); Sleep, D. et al., *Saccharomyces cerevisiae Strains that Over Express Heterologous Proteins*, Bio/Technol. 9: 183-187 (1991); Bischoff et al., *Purification & Biochemical Characterization of Recombinant Alpha* 1Antitrypsin Variant Expressed in *Escherichia coli*, Biochemistry 30:3464-3472 (1991)).

In particular embodiments of the invention, the level of des-lys A1PI in the final preparation is controlled by modulating the ethanol content of the Cohn IV-1 precipitate or the Cohn IV-1+IV-4 precipitate. In some embodiments of the invention in which the level of des-lys A1PI is increased, the ethanol content is increased by treating the precipitate with ethanol in a concentration between 10% and 50%, or between 30% and 50%, or between 35% and 45%, or about 40%. In some other embodiments of the invention in which the level of des-lys A1PI is decreased, the ethanol content is maintained below 10%. In other embodiments of the invention in which the level of des-lys A1PI is increased, an A1PI containing composition, such as the precipitate, is treated under an appropriate ethanol concentration with a basic carboxypeptidase, such as carboxypeptidase N(CPN[23]; EC 3.4.17.3), carboxypeptidase U (CPU[24]; EC 3.4.17.20), carboxypeptidase M (CPM[25]; EC 3.4.17.12) and carboxypeptidase B (CPB[26]; EC 3.4.17.2)

IV. A1PI Activity Assays

In one embodiment, a chromogenic assay is used to detect A1PI activity. The assay utilizes a trypsin sensitive chromogenic substrate which releases p-nitroaniline in the presence of trypsin (supplied by Sigma Chemical Co. of St Louis, Mo.). The p-nitroaniline released is detected at 405 nm. A1PI inhibits the release of p-nitroaniline from the substrate. The activity of A1PI in the product can be determined by reference to a standard A1PI activity curve. Other assays are known in the art and can be used to evaluate activity.

V. Protein Content

Protein content is determined by a BIO-RAD assay method utilizing differential color change of a Coomassie Blue dye in response to various concentrations of protein measured at 595 nm. The protein content is calculated from a standard curve. Other assays are known in the art and can be used to determine protein content.

VI. Administration

A1PI is infused into a patient at a rate of about 0.08 ml/kg body weight per minute for the first 10 minutes. If the patient does not experience any discomfort, the rate is increased as tolerated. If tolerated, subsequent infusions to the same patient may be at the higher rate. If adverse events occur, the rate should be reduced or the infusion interrupted until the symptoms subside. The infusion may then be resumed at a rate which is tolerated by the patient. If large doses are to be administered, several reconstituted vials of A1PI may be pooled in an empty, sterile I.V. infusion container using aseptic technique.

In another embodiment, A1PI can be administered nasally and/or orally, by inhaling from a nebulizer or similar apparatus.

VII. EXAMPLES

Example 1

A. Results

IEF Isoform Band Pattern of Human A1PI

The IEF isoform band pattern of human plasmatic A1PI is determined mostly by the neuraminic acid content of their 3 N-linked carbohydrates[5-8] and by the extent of C-terminal Lys truncation[17,18]. M4 and M6 are the predominant bands in plasma and in the licensed A1PI product Prolastin® (Alpha$_1$-Proteinase Inhibitor (Human)). They contain two biantennary and one triantennary sugar side chain(s) (M4) or three biantennary sugar structures (M6) (FIG. 1). In the case of Aralast® (Alpha$_1$-Proteinase Inhibitor (Human)) minor amounts of the M4 and M6 bands were still visible and the major bands, which were slightly less acidic than the original M2 and M4 bands, were visible in the M2 and M4 region. As the ratio of different complex sugar structures in all products were almost identical, a C-terminal Lys truncation was identified as the cause for this anodal band shift[17,18].

We found that basic carboxypeptidases such as carboxypeptidase N(CPN[23]; EC 3.4.17.3), carboxypeptidase U (CPU[24]; EC 3.4.17.20), carboxypeptidase M (CPM[25]; EC 3.4.17.12) and carboxypeptidase B (CPB[26]; EC 3.4.17.2) could indeed cleave off C-terminal lysine from a non-cleaved A1PI product. C-terminal lys removal was particularly observed when the A1PI preparation had been in temporary contact with 40% ethanol followed by dilution to 10% ethanol (CPN, CPU, CPM, CPB) or when A1PI was incubated with the carboxypeptidase in the presence of only 10% ethanol (CPB and slightly for CPN) (FIG. 1). Carboxypeptidase treatment in the absence of ethanol did not induce a shift of the major IEF bands M6 and M4 to the M4 and M2 region, respectively. Whereas CPB, CPU and CPM caused almost complete Lys truncation of A1PI that had been in temporary contact with 40% ethanol, only ~60% truncation was observed with CPN, a level which is characteristic for Aralast® (Alpha$_1$-Proteinase Inhibitor (Human)).

Figure 2B:
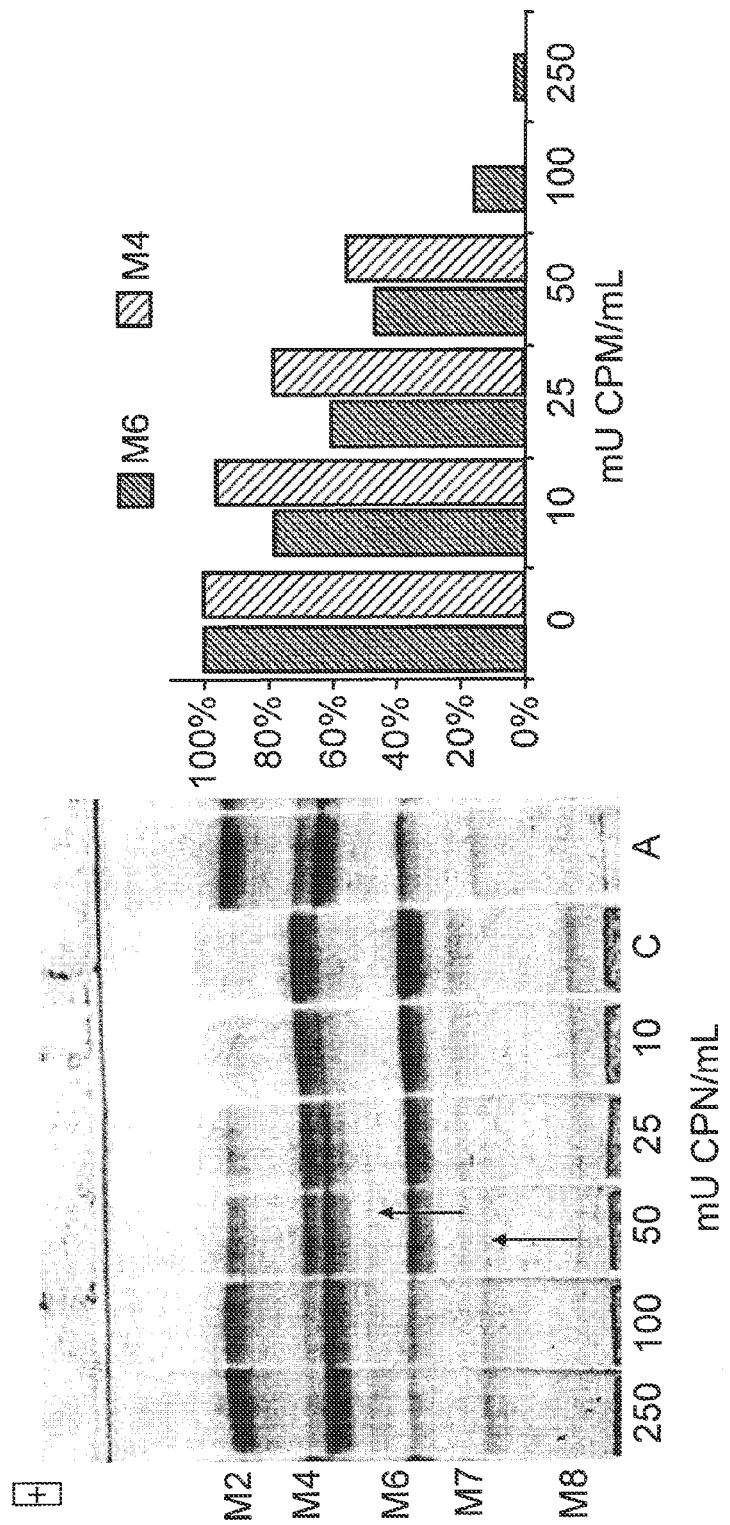

The concentration dependency of C-terminal Lys truncation of 40% ethanol-pretreated purified A1PI was determined for CPN and CPM. We found that 50 mU CPM/ml or between 50 and 270 mU CPN/ml could induce 50% C-terminal A1PI truncation (FIG. 2A+B). For comparison, about 65 mU CPN/ml[27] is detected in plasma corresponding to a plasma concentration of 30 µg/mL, 40 mU/ml in the starting material of the Cohn fractionation process and a similar amount of CPN is present in the starting material of Aralast® (Alpha$_1$-Proteinase Inhibitor (Human)). An anodic shift of the A1PI isoforms M7 and M8 was also induced by CPM (FIG. 2B).

A1PI in Ethanol Precipitates or Pastes

Purified A1PI preparations and A1PI present in dissolved alcohol precipitates, which are the starting material for all plasmatic A1PI downstream processes, appeared to have a similar ethanol dependence of Lys truncation by carboxypeptidases.

So-called Cohn IV-1 precipitate[28] was the starting material for A1PI products with a plasma-like IEF pattern. Cohn IV-1 precipitate is usually derived after ethanol fractionation of plasma by precipitation with 20% ethanol at pH 5.2.

A somewhat different alcohol precipitation was used for Aralast® (Alpha$_1$-Proteinase Inhibitor (Human)). After initial precipitation of plasma with 20% ethanol at pH 5.2, the precipitate (the so-called IV-1 paste) was not removed and the 20% ethanol-containing plasma suspension was adjusted to pH 5.9 and then to 40% ethanol, which resulted in a second precipitation (the so-called IV-4 paste). The total precipitate, the ($IV_{1+4}$) paste, was collected and served as the starting material for the Aralast® ($Alpha_1$-Proteinase Inhibitor (Human)) process.

Based on our experiences with purified A1PI, prior exposure of $IV_{1+4}$ paste to 40% ethanol might have caused the truncation in the subsequent extraction step. This hypothesis was therefore tested with IV-1 paste which contained almost identical levels of CPN (59 mU/ml) compared to $IV_{1+4}$ paste (61 mU/ml, both normalized to direct paste extract with 7 volumes).

IV-1 paste was dissolved in buffer at pH 8.8 and was temporarily exposed to 40% ethanol, diluted to 10% ethanol and then stored during 6 hours (40=>10% EtOH). This procedure was sufficient for C-terminal Lys truncation at a level similar to Aralast® ($Alpha_1$-Proteinase Inhibitor (Human)) and was apparently induced by the CPN present in the paste (FIG. 3). Temporary contact of dissolved IV-1 paste with 10% ethanol did not result in Lys truncation. The Lys truncation induced by the procedure used (40=>10% EtOH) could be inhibited by 6-amino caproic acid[29] and dose-dependently by DL-2-mercaptomethyl-3-guanidinoethylthio-propanoic acid, a more specific CPN-inhibitor[30] (CPU Ki=0.20 µM; CPN Ki=0.0087 µM[31]).

As observed for purified A1PI (FIG. 1) CPB added to dissolved IV-1 paste could also induce almost complete Lys truncation in the presence of only 10% ethanol, whereas the CPN present in the paste (in the absence of CPB) did not remove the C-terminal lysine in the presence of 10% ethanol (data not shown).

Ethanol Dependency of Lys Truncation in Purified A1PI

Figure 4:
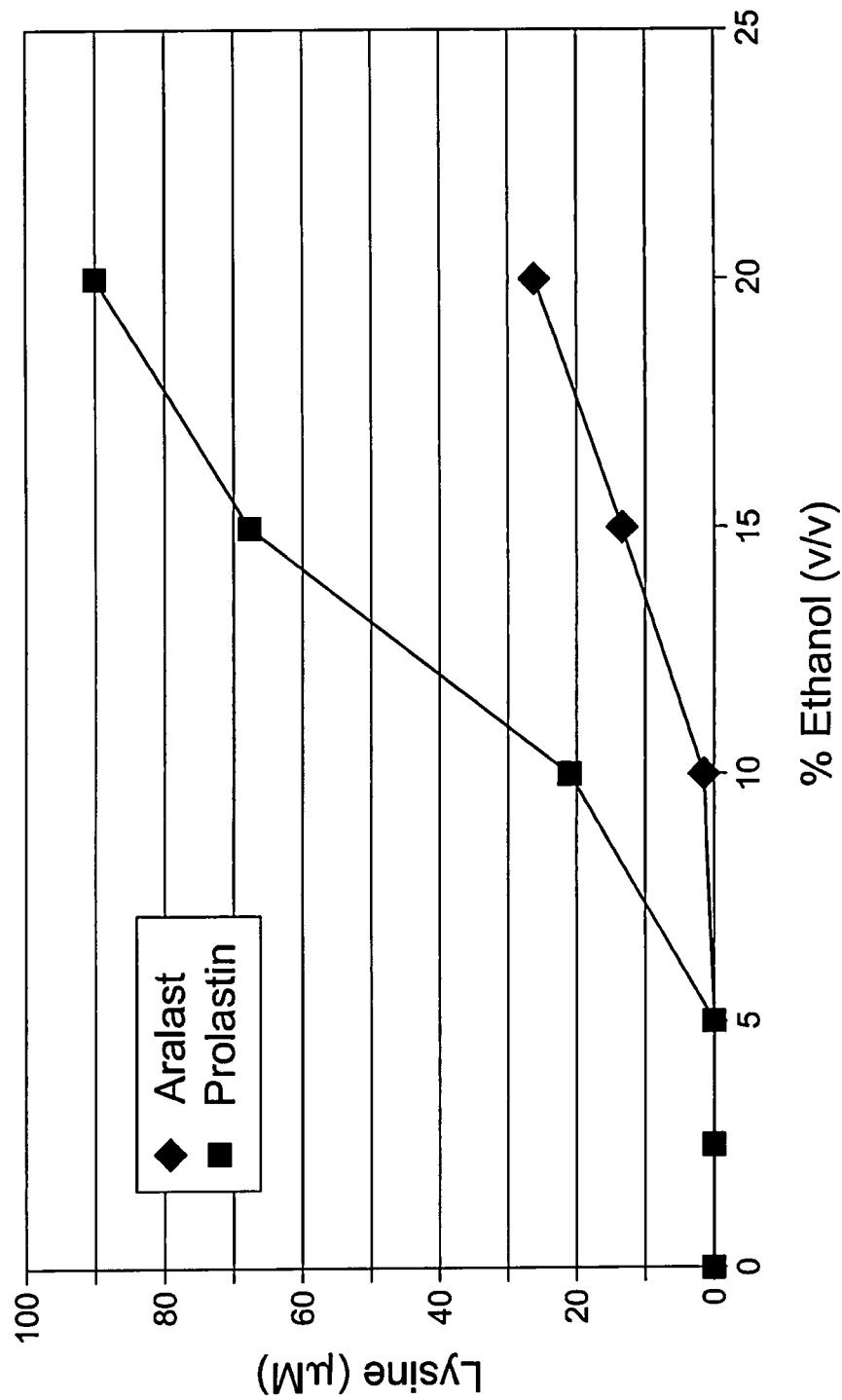
FIG. 4: Effect of ethanol on the CPN-catalysed removal of C-terminal lysine from A1PI. Prolastin® (Alpha$_1$-Proteinase Inhibitor (Human)) or Aralast® (Alpha$_1$-Proteinase Inhibitor (Human)) were mixed with different ethanol concentrations and incubated with CPN during 10 min. Released lysine was quantified by RP-HPLC relative to an internal standard.

Lys truncation in purified A1PI was also measured by quantification of released Lys using a HPLC method. This is a sensitive method that was used to determine the alcohol dependence of Lys truncation of Prolastin® ($Alpha_1$-Proteinase Inhibitor (Human)) or Aralast) ($Alpha_1$-Proteinase Inhibitor (Human)) by CPN. Both A1PI products showed a linear increase of Lys removal with increasing ethanol concentration starting at 5% ethanol for Prolastin® ($Alpha_1$-Proteinase Inhibitor (Human)) and at 10% for Aralast® ($Alpha_1$-Proteinase Inhibitor (Human)) (FIG. 4). Differences in the ethanol dependency between the products apparently reflects their different starting level of truncation. This method also showed that very small amounts of Lys were removed from Prolastin® ($Alpha_1$-Proteinase Inhibitor (Human)) in the absence of ethanol.

Apart from the possible influence of ethanol on A1PI, a direct effect of ethanol on CPN, i.e. on the rate of the substrate (Bz-Gly-Arg) cleavage could be detected, which almost doubled at 10% ethanol (FIG. 5). This effect was reversible and completely disappeared after dilution.

BAL Samples

Figure 6A:
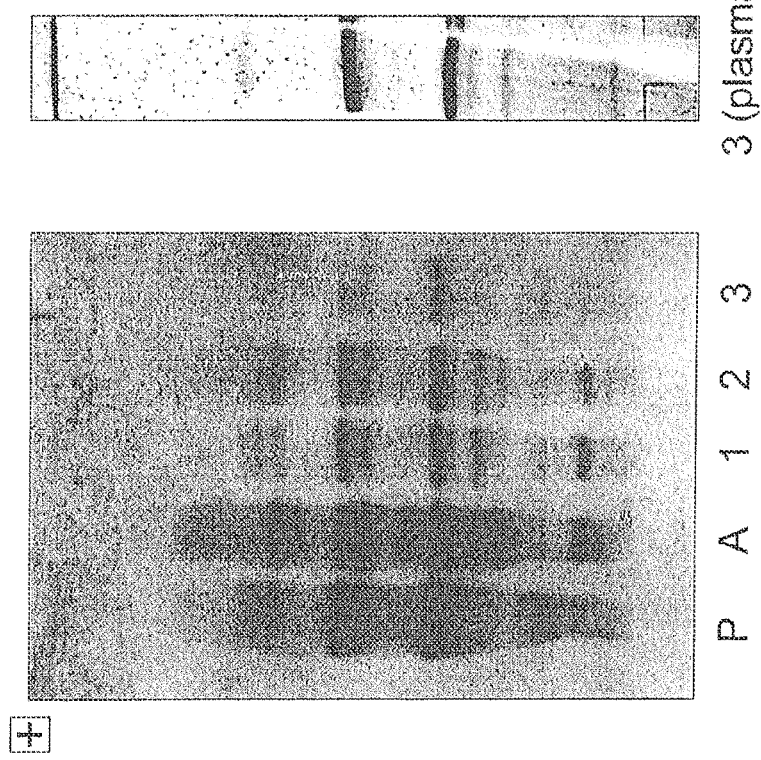

Bronchio-alveolar lavage (BAL) fluid was isolated from patients who had not received A1PI augmentation therapy. BAL samples, which were characterized by high resolution IEF, showed the IEF pattern characteristic for C-terminal lysine removal but at a lower level than that in Aralast® ($Alpha_1$-Proteinase Inhibitor (Human)) (FIG. 6). This suggests that CPM present in lung tissue[32] might have been responsible for the lysine removal under physiologic conditions. A corresponding plasma sample did not show this partial Lys truncation.

The Lys-cleavage of A1PI in BAL samples was confirmed by MS analysis of tryptic peptides, which demonstrated that the C-terminal lysine was removed from the A1PI C-terminal peptide at 657 m/z.

B. Discussion

Contributors to the heterogeneity of a biological product can include biosynthetic mechanisms used by living organisms, manufacturing processes, and storage conditions. Heterogeneity in plasma-derived therapeutic proteins is only slightly affected by contributions from individual donor variations because of the dilution effect provided by the large plasma pool size of several thousand donors.

We have shown that large-scale manufacturing conditions of A1PI cause primary sequence modifications of A1PI resulting in structural heterogeneity. Fractionation with cold ethanol[28] used in the large-scale manufacturing of A1PI facilitates removal of the C-terminal lysine from the A1PI molecule by carboxypeptidases. The loss of approximately 60% of the total C-terminal lysine content of A1PI in Aralast® ($Alpha_1$-Proteinase Inhibitor (Human)) gives the molecule an extra negative charge causing an unusual mobility of the glycolsoforms with an anodal shift on IEF gels. Differences in the extent of C-terminal lysine truncation between the commercial products is due to variations in the manufacturing conditions exposing A1PI to different ethanol concentrations, and not to differences in the concentration of carboxypeptidases present in the various intermediate fractions. Prolastin® ($Alpha_1$-Proteinase Inhibitor (Human)), which has a C-terminal truncation of about 2%, is purified from fraction IV-1: this fraction is obtained by precipitation of fraction I supernatant with 20% ethanol. Aralast ($Alpha_1$-Proteinase Inhibitor (Human)) is obtained from fraction IV-1+IV-4, which is made by increasing the ethanol concentration of fraction IV-1 to 40%, without preceding removal of the precipitate. Prior exposure to high concentrations of ethanol is required to make A1PI more susceptible to carboxypeptidases.

The data presented support the hypothesis that A1PI has first to be altered by temporary exposure to 40% ethanol before the C-terminal lysine becomes susceptible to the action of basic carboxypeptidases to a major extent. In contrast, many other proteins can be C-terminal truncated under physiological conditions without prior alteration (probably conformational change) of the protein (immunoglobulin[33,34], alpha2 antiplasmin[35], erythropoietin[36], hemoglobin[37], creatine kinase[38], enolase[39], complement factor[40], albumin[41], tissue plasminogen activator[19], stromal cell-derived factor 1 alpha[42]). The alteration of A1PI induced by temporary exposure to 40% ethanol persists even after dilution to 10% ethanol (FIG. 3). Exposure of A1PI to only 10% ethanol is not sufficient to release a major amount of C-terminal lysine by the action of CPN required to produce a visible anodal shift of glycolsoforms. Only the small 35 kDa carboxypeptidase B from pancreas, which is not found in plasma, was able to completely truncate A1PI in the presence of 10% ethanol.

The ethanol-induced structural alteration of A1PI may also be responsible for the different behavior of alcohol precipitates IV-1 and IV-1+4 as starting material of an otherwise almost identical A1PI downstream process. IV-1+4 paste, which has been in contact with 40% ethanol, yields a final product with ~60% lysine truncation, whereas IV-1 paste, generated with 20% ethanol, after using identical downstream processing steps, yields a final A1PI product with only 2% lysine truncation (qualitatively shown in FIG. 1, Control; compare A with C).

In a purified system, CPN in a dose-dependent fashion changed the glycolsoform pattern of A1PI made from fraction IV-1 into a band pattern identical to that of A1PI made from IV-1+4. The pronounced anodal shift of the original M6 and M4 bands to the M4 and M2 region is mainly caused by temporary exposure of A1PI to 40% ethanol.

In plasma, only 2 basic carboxypeptidases are known: CPN, which is constitutively active, and proCPU, which requires proteolytic activation. CPN is probably the carboxypeptidase responsible for the A1PI C-terminal truncation during extraction of the various pastes. CPN is found in similar amounts in all alcohol precipitates studied and the lysine removal from A1PI can be completely inhibited by addition of 100 mM 6-aminocaproic acid or by the more CPN-specific inhibitor 2-mercaptomethyl-3-guanidinoethylthiopropanoic acid[30] at 10 µmol/l[43].

However, CPU is not stable during incubation at 37° C. for 1 h, whereas the carboxypeptidase that is responsible for A1PI truncation withstands such treatment.

This finding of almost complete inhibition of truncation demonstrates that no truncation has taken place during ethanol fractionation, as lysine removal requires both prior exposure of A1PI to ethanol as well as a pH>5.9 to provide optimal conditions for CPs activity.

CPN is a zinc-dependent metalloproteinase that is synthesized in the liver and secreted into the blood. It is a glycoprotein that consists of two 83-kDA regulatory subunits and two 50-kDA catalytic subunits which form a stable tetramer of 280-kDa[44]. CPN was originally identified to be responsible for inactivating bradykinin by removal of C-terminal arginine. CPN also removes C-terminal arginines from the anaphylatoxins C3a, C4a, and C5a with subsequent reduction of their biological activity[40]. Creatine kinase MM, an intracellular enzyme that mediates the transfer of a phosphate group from adenosine triphosphate to creatinine, is another substrate for CPN. CPN cleaves C-terminal lysines from CK-MM to generate CK-MM1 and CK-MM2[45]. The CPN activity in plasma is about 65 mU/ml which is sufficient for lysine removal from several important physiological proteins like erythropoietin[36], hemoglobin[46], stromal cell-derived factor-1-alpha[47], complement proteins[40], albumin[41] and probably many other proteins with a basic C-terminus. 50 mU CPN/ml cleave a 10-20% of the C-terminal lysines from purified uncleaved A1PI (FIG. 2).

On the other hand, using a direct measurement of lysine cleavage, we demonstrated that CPN is able to remove lysine to a small extent even in the absence of ethanol, and that this reaction can be enhanced by ethanol. However, the small amount of des-Lys A1PI formed in the absence of ethanol probably escapes visualization on IEF gels due to limits in the resolution. Apart from having an influence on the substrate, ethanol seems also to directly affect carboxypeptidase activity. Increasing the ethanol concentration, linearly increases CPN activity (measured with Hip-Arg) resulting in a doubled CPN activity at a final ethanol concentration of 10%. An effect of ethanol on CPB activity toward small synthetic substrates also has been described[48].

Although with the current methods we were unable to show that the des-Lys form of A1PI is present in plasma, A1PI recovered from human BAL samples consists in part of the des-Lys form. This is most likely due to the action of CPM which is highly expressed in lung tissue[32], and CPM activity is also found in bronchio-alveolar fluid[49]. We speculate that A1PI is exposed to CPM when it diffuses through lung tissue from the vasculature into the alveolar space. CPM, attached to lung membranes by a phosphatidylinositol anchor is also found in alveolar type 1 cells, which comprise about 9% of total human lung cells and 93% of total alveolar epithelial surface area[32]. Type I cells, together with basement membrane and capillary endothelial cells, function primarily as a thin, gas-permeable membrane between air and blood.

In summary, we have identified the cause of C-terminal truncation of A1PI present in products used for augmentation therapy and shown that A1PI becomes a substrate for carboxypeptidase, specifically CPN, due to the exposure of A1PI to ethanol during Cohn fractionation. In search for a naturally occurring des-Lys form of A1PI we discovered the presence of this modification in BAL from patients who had not been treated with any of the products.

Methods

Reagents

Carboxypeptidase B (Sigma), carboxypeptidase N (Elastin Company), carboxypeptidase U (proCPU, purified and activated according to the protocol described[50]) and a recombinant carboxypeptidase M expressed in *P. pastoris*, and purified as described[51] were used. The commercially available A1PI concentrates, Aralast® (Alpha$_1$-Proteinase Inhibitor (Human)) and Prolastin® (Alpha$_1$-Proteinase Inhibitor (Human)), lot numbers LH020A31 and PR4HA43, respectively, as well as a purified A1PI preparation (prepared according to the ARALAST® (Alpha$_1$-Proteinase Inhibitor (Human)) process but with IV-1 paste as starting material) were used. The various reagents used will be described below. Unless stated otherwise, reagents of the highest purity available were used.

Measurement of Basic Carboxypeptidases

The activity of the basic carboxypeptidases was measured with a HPLC-assisted assay as described[52]. This assay is based on the cleavage of the synthetic substrate hippuryl-L-arginine. Released hippuric acid was determined with reverse phase high performance liquid chromatography (RP-HPLC). Briefly, to 10 µl of sample, 40 µl of 30 mM hippuryl-L-arginine (Bachem Feinchemikalien, Buchs, Switzerland) in 50 mM HEPES, pH 8.0, was added and incubated for 30 minutes at 37° C. in a water bath. Hippuryl-L-arginine cleavage was stopped by adding 50 µl of 1 M HCl. 10 µl of o-methyl hippuric acid (synthesized from methylbenzoyl chloride) serving as an internal standard was added afterwards. The hippuric acid (Bz-Gly, Fluka, Buchs, Switzerland) and o-methyl hippuric acid were extracted with ethyl acetate (300 µl). This layer was evaporated to dryness, redissolved in the mobile phase (10 mM KH$_2$PO$_4$, 10% acetonitrile, pH 3.5) and injected unto the column (C-18 Chromolith, performance 100-4.6 mm column (Merck, Darmstadt, Germany). The separation was done in isocratic mode and monitored at 228 nm. One unit of carboxypeptidase activity is defined as the amount of enzyme required to release 1 µmol of hippuric acid per min at 37° C. under the assay conditions described.

Incubation with CPs and Analysis by IEF

A1PI solutions were incubated with different CPs. Temporary exposure to 40% ethanol was achieved by diluting the A1PI preparation (38 µM) with 96% ethanol. The precipitate formed was kept 30 min at −20° C. and a further 30 min at +4° C., before it was diluted with TRIS-HCl buffer (pH 8.8) to a final concentration of 10% ethanol. Concomitantly, CPs were added with the TRIS buffer and the reaction mixture containing 10 µM A1PI was then incubated at 37° C. for 60 min. Before IEF analysis dithioerythritol (DTE) was added to a final concentration of 5 mM. In addition, the incubation with CPs was done without ethanol or at 10% ethanol. Furthermore, we ran two concentration rows with either CPN (270-1 mU/ml) or CPM (250-10 mU/ml) after temporary exposure of A1PI to 40% ethanol (CPN units were tested against Hip-Arg).

HPLC Method for Determination of Liberated Lysine

The cleaved C-terminal lysine of A1PI was determined using automated orthophtalicdialdehyd (OPA) pre-column derivatization and high-performance liquid chromatography. The derivatization reagent was prepared by dissolving 100 mg of OPA in 2.5 mL of methanol by short ultrasonication, adding 23 mL of deoxygenated sodium borate buffer (0.2 mol/L, pH 9.0), 100 µl of 2-mercaptoethanol and 100 µl of Brij 35 as described[53]. The system used was an ASTED HPLC system (Gilson, Paris) with Shimadzu RF-A fluorescence detector and a C-18 Chromolith ODS 4.7*100 mm column. A mixture of 50 mM $KH_2PO_4$, acetonitrile and methanol (ratio 50:24:26) was used as mobile phase and ornithine was used as internal standard.

To 30 µl 0.5 mM A1PI (using ARALAST® (Alpha$_1$-Proteinase Inhibitor (Human)) or PROLASTIN® (Alpha$_1$-Proteinase Inhibitor (Human)) 10 µl water or ethanol (different concentrations) was added. Afterwards 10 µl CPN (500 U/L) was added and after a 10 minutes incubation interval the reaction was stopped by adding 50 µl internal standard in 0.25 M HCl. The cleaved lysine was quantified as described above. The assay demonstrated good linearity between 2-120 µM final concentrations of Lys.

Effect of Ethanol on the Activity of Purified and Plasma CPN

The effect of increasing concentrations of ethanol on CPN activity was tested as follows. To 10 µl purified CPN or plasma 10 µl ethanol (0-40%, maximum final concentration therefore 20%) was added and directly incubated with 30 µl substrate (30 mM Hip-Arg pH 8.0) for 20 minutes and activity was quantified as described above.

Extraction of Pastes
40%=>10% EtOH:

Cohn IV-1 paste was dissolved in 2.6 volumes of 10 mM Tris-buffer at pH 8.8 and incubated for 30 min at 22° C. The suspension was made 40% in ethanol (by addition of 2.4 volumes of ethanol), stirred for a further 60 min, diluted with the same Tris-buffer to 10% ethanol and extracted for a further 6 h.

10% EtOH:

IV-1 paste was dissolved in 20.6 volumes of 10 mM Tris-buffer at pH 8.8 and incubated during 30 min at 22° C. The suspension was made 10% in ethanol (by addition of 2.4 volumes of ethanol) and stirred for a further 6 h at 22° C. and pH 8.8.

The following inhibitors were added in parallel during extraction and dilution with Tris-buffer: 100 mM 6-aminocaproic acid, 10 µM or 1 nM 2-mercaptomethyl-3-guanidinoethylthiopropanoic acid (a more specific inhibitor of CPN). The samples were characterized by high resolution isoelectric focusing.

Comparison of Different Pastes:

Pastes were dissolved in 24 volumes (potential presence of filter aid was ignored) of 30 mM Tris/HCl buffer (pH 10.4), adjusted to pH 8.5 and stirred for 2 h at 4° C. and 1.5 h at 40° C. and cooled again to 20° C. Samples could be frozen and stored at −20° C.

Isoelectric Focusing

For high resolution isoelectric focusing a new hybrid IEF method using IPG-Immobiline gels (GE Healthcare Bio-Sciences, pI 4.2-4.9, Uppsala, Sweden) was developed which is similar to that described by Weidinger[54]. Samples were diluted with water to 0.5 mg A1PI/mL and 5 mM DTE was added. Samples (20 µl) were applied close to the cathode on the pre-focused gel and focused for 150 min (5000 Vh). For paste extracts focusing time was extended to 420 min. Gels were stained with Coomassie Brilliant Blue G-250 (BioRad, Hercules, USA) as described by Neuhoff[55]. Blotting and immunostaining were done with a rabbit anti-A1PI antibody (Rabbit Anti-Human Alpha-1-Antitrypsin, #A0012, DakoCytomation, Glostrup, Denmark).

BAL Samples

BAL samples from patients with chronic obstructive pulmonary disease (COPD) or cancer were provided by Prof. R. Sakalauskas, Vilnius, Lithuania. Informed consent was obtained from these individuals. Only samples with A1PI concentrations higher than 2 µg/mL were further investigated.

Isolation and MS Analysis of A1PI from BAL Fluid

To concentrate the proteins before SDS-PAGE, BAL samples were subjected to a solid phase extraction (SPE) cartridge containing a C4 gel (Macherey-Nagel, Düren, Germany). The SPE cartridge was primed with 1 mL acteonitrile followed by 1 mL of water. All solvents used for priming, washing and elution of proteins contained 0.1% formic acid. The BAL sample was loaded and the column was subsequently washed with 1 mL of water. Elution of proteins was achieved by applying 500 µl of 40% acetonitrile. The eluates were dried in a SpeedVac concentrator. The dry samples were solved in 15 µl of SDS-PAGE loading buffer and then subjected to SDS-PAGE under reducing conditions[8]. Coomassie-stained bands were de-stained, carbamidomethylated, digested with trypsin and extracted from gel pieces. The extracts were dried in a SpeedVac concentrator and reconstituted with water containing 0.1% formic acid before LC-MS analysis. MS and MSMS analysis was performed as described previously. For every sample, both a MS and tandem MS run were performed.

Example 2

Isoelectric focusing (IEF) of alpha(1)-proteinase inhibitor (A1PI) shows that commercial products and plasma have different glycolsoform band patterns. Those in Aralast® (Alpha$_1$-Proteinase Inhibitor (Human)) reflect an anodal shift of glycolsoforms. The protein, including glycoproteomic analyses, and structural features of A1PI products were investigated by state-of-the-art techniques.

Aralast® (Alpha$_1$-Proteinase Inhibitor (Human), Prolastin® (Alpha$_1$-Proteinase Inhibitor (Human)), and Zemaira® (Alpha$_1$-Proteinase Inhibitor (Human)) were analyzed by high-resolution IEF and high-performance size-exclusion chromatography (HP-SEC). Preparative separated isoforms from IEF were further purified by chromatography and subjected to mass spectrometry for sequence analyses, peptide mapping, and glycosylation analysis. Deamidation was quantified by enzymatic isoaspartate detection. Multiple sequence alignments and structural bioinformatics analyses were performed.

In HP-SEC, Prolastin® (Alpha$_1$-Proteinase Inhibitor (Human)) had the highest aggregate content at approximately 30 percent. Isoforms from all products purified by high-resolution IEF were sequenced with an amino acid coverage of more than 98 percent. Deamidation of Asn 116 and Asn314 in A1PI was to found to some extent in all products and confirmed quantitatively by enzymatic analysis. There were no signs of methionine oxidation. Cys232 was found to be cysteinylated in A1PI in Prolastin® (Alpha$_1$-Proteinase Inhibitor (Human)) and Aralast® (Alpha$_1$-Proteinase Inhibitor (Human)) as in plasma, but not in Zemaira® (Alpha$_1$-Proteinase Inhibitor (Human)). All products showed truncation of the C-terminal lysine. Intact A1PI concentrates contained mainly diantennary, disialylated and smaller amounts of triantennary, trisialylated N-glycans. The percentage of fucosylation was similar in all products. Site-specific glycan analysis revealed bands M6 contained only diantennary glycans, whereas the more acidic bands M4 and M2 also carried triantennary structures. The most acidic isoforms, M2 in Prolastin® (Alpha₁-Proteinase Inhibitor (Human)) and Zemaira® (Alpha₁-Proteinase Inhibitor (Human)) and M0 in Aralast® (Alpha₁-Proteinase Inhibitor (Human)) additionally exhibited tetraantennary N-glycans.

Protein chemical characterization of A1PI showed that all A1PI products to some extent differ from A1PI circulating in human plasma. Bioinformatic analysis indicated that removal of C-terminal Lys394 and cysteinylation of Cys232 are unlikely to affect structure and/or function of A1PI but cysteinylation may influence interaction between A1PI and its physiologic ligands. Lack of cysteinylation may cause a protein to dimerize. Aralast® (Alpha₁-Proteinase Inhibitor (Human)). Prolastin® (Alpha₁-Proteinase Inhibitor (Human)) and Zemaira® (Alpha₁-Proteinase Inhibitor (Human)) contain the same set of N-glycans in the same ratios as those in normal human plasma A1PI. Tri- and tetraantennary structures are responsible for the partitioning into IEF isoforms, with the migration shift of Aralast® (Alpha₁-Proteinase Inhibitor (Human)) not being due to any difference in the N-glycosylation, but to the partial loss of the C-terminal lysine (des-Lys A1PI).

REFERENCES

1. Carrell, R. W., Jeppsson, J. O., Laurell, C. B., Brennan, S. O., Owen, M. C., Vaughan, L., & Boswell, D. R. Structure and variation of human alpha 1-antitrypsin. *Nature* 298, 329-334 (1982).
2. Carrell, R. W., Jeppsson, J.-O., Vaughan, L., Brennan, S. O., Owen, M. C., & Boswell, D. R. Human alpha 1 antitrypsin: Carbohydrate attachment and sequence homology. *FEBS Lett.* 135, 301-303 (1981).
3. Jeppsson, J.-O. & Franzen, B. Typing of genetic variants of alpha 1-antitrypsin by electrofocusing. *Clin. Chem.* 28, 219-225 (1982).
4. Brantly, M. in Alpha 1 antitrypsin Deficiency. ed. Crystal, R. G. 45-59 (New York; 1996).
5. Mills, P. B., Mills, K., Johnson, A. W., Clayton, P. T., & Winchester, B. G. Analysis by matrix assisted laser desorption/ionisation-time of flight mass spectrometry of the post-translational modifications of alpha 1-antitrypsin isoforms separated by two-dimensional polyacrylamide gel electrophoresis. *Proteomics.* 1, 778-786 (2001).
6. Vaughan, L., Lorier, M. A., & Carrell, R. W. alpha 1-Antitrypsin microheterogeneity. Isolation and physiological significance of isoforms. *Biochim. Biophys. Acta* 701, 339-345 (1982).
7. Mills, K., Mills, P. B., Clayton, P. T., Mian, N., Johnson, A. W., & Winchester, B. G. The underglycosylation of plasma alpha 1-antitrypsin in congenital disorders of glycosylation type I is not random. *Glycobiology* 13, 73-85 (2003).
8. Kolarich, D., Weber, A., Turecek, P. L., Schwarz, H.-P., & Altmann, F. Comprehensive glyco-proteomic analysis of human alpha-1 antitrypsin and its charge isoforms. *Proteomics* (2006, in press).
9. Jeppsson, J. O., Lilja, H., & Johansson, M. Isolation and characterization of two minor fractions of alpha 1-antitrypsin by high-performance liquid chromatographic chromatofocusing. *J. Chromatogr.* 327, 173-177 (1985).
10. Needham, M. & Stockley, R. A. Alpha 1-antitrypsin deficiency. 3: Clinical manifestations and natural history. *Thorax* 59, 441-445 (2004).
11. Abusriwil, H. & Stockley, R. A. Alpha-1-antitrypsin replacement therapy: current status. *Curr. Opin. Pulm. Med.* 12, 125-131 (2006).
12. Hein, R. H., Van Beveren, S. M., Shearer, M. A., Coan, M. H., & Brockway, W. J. Production of alpha 1-proteinase inhibitor (human). *Eur. Respir. J [Suppl.]* 9, 16s-20s (1990).
13. Stoller, J. K., Rouhani, F., Brantly, M., Shahin, S., Dweik, R. A., Stocks, J. M., Clausen, J., Campbell, E., & Norton, F. Biochemical efficacy and safety of a new pooled human plasma alpha(1)-antitrypsin, Respitin. *Chest* 122, 66-74 (2002).
14. Cowden, D. I., Fisher, G. E., & Weeks, R. L. A pilot study comparing the purity, functionality and isoform composition of alpha-1-proteinase inhibitor (human) products. *Curr. Med. Res. Opin.* 21, 877-883 (2005).
15. Taniguchi, T., Rolf, J. M., Bhattacharya, P., and Uemura, Y. Process for separating alpha-1 proteinase inhibitor from Cohn fraction IV-1 and IV-4 paste. Alpha Therapeutic Corporation. PCT/US95/07616[WO 95/35306], 1-28. 28-12-1995. 16-6-1995.
16. Kee, S. M., Cook, P. I., Smith, J. R., Kling, R., Fowler, S. A., and Weber, D. Method for Purification of Alpha-1-Antitrypsin. Aventis Behring, L. L. C. [WO 2004/060528 A1]. 22-7-2004. 19-12-2003.
17. Turecek, P. L., Weber, A., Mitterer, A., Graninger, M., Kolarich, D., Altmann, F., Matthiessen, H. P., Nicolaes, G. A. F., & Schwarz, H.-P. Biochemical and molecular characterization of alpha1-proteinase inhibitor products used for replacement therapy. *Transfusion* (2006, submitted).
18. Kolarich, D., Weber, A., Turecek, P. L., Schwarz, H.-P., & Altmann, F. Glycoproteomic analyses of human Alpha1-antitrypsin from commercially available concentrates. *Transfusion* (2006, submitted).
19. Harris, R. J. Processing of C-terminal lysine and arginine residues of proteins isolated from mammalian cell culture. *J. Chromatogr. A* 705, 129-134 (1995).
20. Bokisch, V. A. & Muller-Eberhard, H. J. Anaphylatoxin inactivator of human plasma: its isolation and characterization as a carboxypeptidase. *J. Clin. Invest* 49, 2427-2436 (1970).
21. Redlitz, A., Tan, A. K., Eaton, D. L., & Plow, E. F. Plasma carboxypeptidases as regulators of the plasminogen system. *J. Clin. Invest* 96, 2534-2538 (1995).
22. Skidgel, R. A., Johnson, A. R., & Erdos, E. G. Hydrolysis of opioid hexapeptides by carboxypeptidase N. Presence of carboxypeptidase in cell membranes. *Biochem. Pharmacol.* 33, 3471-3478 (1984).
23. Plummer, T. H., Jr. & Hurwitz, M. Y. Human plasma carboxypeptidase N. Isolation and characterization. *J. Biol. Chem.* 253, 3907-3912 (1978).
24. Schatteman, K. A., Goossens, F. J., Scharpe, S. S., & Hendriks, D. F. Proteolytic activation of purified human procarboxypeptidase U. *Clin. Chim. Acta* 292, 25-40 (2000).
25. Skidgel, R. A., Davis, R. M., & Tan, F. Human carboxypeptidase M. Purification and characterization of a membrane-bound carboxypeptidase that cleaves peptide hormones. *J. Biol. Chem.* 264, 2236-2241 (1989).
26. Brodrick, J. W., Geokas, M. C., & Largman, C. Human carboxypeptidase B. II. Purification of the enzyme from pancreatic tissue and comparison with the enzymes present in pancreatic secretion. *Biochim. Biophys. Acta* 452, 468-481 (1976).

27. Hendriks, D., Scharpe, S., & van Sande, M. Assay of carboxypeptidase N activity in serum by liquid-chromatographic determination of hippuric acid. *Clin. Chem.* 31, 1936-1939 (1985).
28. Cohn, E. J., Strong, L. E., Hughes, W. L., Jr., Mulford, D. J., Ashworth, J. N., Melin, M., & Taylor, H. L. Preparation and Properties of Serum and Plasma Proteins. IV. A System for the Separation into Fractions of the Protein and Lipoprotein Components of Biological Tissues and Fluids. *J. Am. Chem. Soc.* 68, 459-475 (1946).
29. George, S., Ishikawa, Y., Perryman, M. B., & Roberts, R. Purification and characterization of naturally occurring and in vitro induced multiple forms of MM creatine kinase. *J. Biol. Chem.* 259, 2667-2674 (1984).
30. Plummer, T. H., Jr. & Ryan, T. J. A potent mercapto bi-product analogue inhibitor for human carboxypeptidase N. *Biochem. Biophys. Res. Commun.* 98, 448-454 (1981).
31. Mao, S. S., Colussi, D., Bailey, C. M., Bosserman, M., Burlein, C., Gardell, S. J., & Carroll, S. S. Electrochemiluminescence assay for basic carboxypeptidases: inhibition of basic carboxypeptidases and activation of thrombin-activatable fibrinolysis inhibitor. *Anal. Biochem.* 319, 159-170 (2003).
32. Nagae, A., Abe, M., Becker, R. P., Deddish, P. A., Skidgel, R. A., & Erdos, E. G. High concentration of carboxypeptidase M in lungs: presence of the enzyme in alveolar type I cells. *Am. J. Respir. Cell Mol. Biol.* 9, 221-229 (1993).
33. Lazar, A. C., Kloczewiak, M. A., & Mazsaroff, I. Matrix-assisted laser desorption/ionization mass spectrometry for the evaluation of the C-terminal lysine distribution of a recombinant monoclonal antibody. *Rapid Commun. Mass Spectrom.* 18, 239-244 (2004).
34. Santora, L. C., Krull, I. S., & Grant, K. Characterization of recombinant human monoclonal tissue necrosis factor-alpha antibody using cation-exchange HPLC and capillary isoelectric focusing. *Anal. Biochem.* 275, 98-108 (1999).
35. Hortin, G. L., Gibson, B. L., & Fok, K. F. Alpha 2-antiplasmin's carboxy-terminal lysine residue is a major site of interaction with plasmin. *Biochem. Biophys. Res. Commun.* 155, 591-596 (1988).
36. Recny, M. A., Scoble, H. A., & Kim, Y. Structural characterization of natural human urinary and recombinant DNA-derived erythropoietin. Identification of des-arginine 166 erythropoietin. *J. Biol. Chem.* 262, 17156-17163 (1987).
37. Michel, B., Igic, R., Leray, V., Deddish, P. A., & Erdos, E. G. Removal of Arg141 from the alpha chain of human hemoglobin by carboxypeptidases N and M. *Circ. Res.* 78, 635-642 (1996).
38. Perryman, M. B., Knell, J. D., & Roberts, R. Carboxypeptidase-catalyzed hydrolysis of C-terminal lysine: mechanism for in vivo production of multiple forms of creatine kinase in plasma. *Clin. Chem.* 30, 662-664 (1984).
39. Wevers, R. A., Boegheim, J. P., Hommes, O. R., van Landeghem, A. A., Mul-Steinbusch, M. W., van der Stappen, J. W., & Soons, J. B. A study on post-synthetic modifications in alfa-alfa enolase (EC 4.2.1.11) brought about by a human serum protein. *Clin. Chim. Acta* 139, 127-135 (1984).
40. Skidgel, R. A. Basic carboxypeptidases: regulators of peptide hormone activity. *Trends Pharmacol. Sci.* 9, 299-304 (1988).
41. Watkins, S., Madison, J., Davis, E., Sakamoto, Y., Galliano, M., Minchiotti, L., & Putnam, F. W. A donor splice mutation and a single-base deletion produce two carboxyl-terminal variants of human serum albumin. *Proc. Natl. Acad. Sci. U.S.A* 88, 5959-5963 (1991).
42. Davis, D. A., Singer, K. E., De La Luz, S. M., Narazaki, M., Yang, F., Fales, H. M., Yarchoan, R., & Tosato, G. Identification of carboxypeptidase N as an enzyme responsible for C-terminal cleavage of stromal cell-derived factor-1 alpha in the circulation. *Blood* 105, 4561-4568 (2005).
43. McGwire, G. B. & Skidgel, R. A. Extracellular conversion of epidermal growth factor (EGF) to des-Arg53-EGF by carboxypeptidase M. *J. Biol. Chem.* 270, 17154-17158 (1995).
44. Levin, Y., Skidgel, R. A., & Erdos, E. G. Isolation and characterization of the subunits of human plasma carboxypeptidase N (kininase i). *Proc. Natl. Acad. Sci. U.S.A* 79, 4618-4622 (1982).
45. Abendschein, D. R. Rapid diagnosis of myocardial infarction and reperfusion by assay of plasma isoforms of creatine kinase isoenzymes. *Clin. Biochem.* 23, 399-407 (1990).
46. Marti, H. R., Beale, D., & Lehmann, H. Haemoglobin Koelliker: a new acquired haemoglobin appearing after severe haemolysis: alpha-2 minus 141 Arg beta-2. *Acta Haematol.* 37, 174-180 (1967).
47. Davis, D. A., Singer, K. E., De La Luz, S. M., Narazaki, M., Yang, F., Fales, H. M., Yarchoan, R., & Tosato, G. Identification of carboxypeptidase N as an enzyme responsible for C-terminal cleavage of stromal cell-derived factor-1 {alpha} in the circulation. *Blood* (2005).
48. Folk, J. E., Wolff, E. C., Schimer, E. W., & Cornfield, J. The kinetics of carboxypeptidase B activity. III. Effects of alcohol on the peptidase and esterase activities; kinetic models. *J. Biol. Chem.* 237, 3105-3109 (1962).
49. Dragovic, T., Schraufnagel, D. E., Becker, R. P., Sekosan, M., Votta-Velis, E. G., & Erdos, E. G. Carboxypeptidase M activity is increased in bronchoalveolar lavage in human lung disease. *Am. J. Respir. Crit. Care Med.* 152, 760-764 (1995).
50. Wang, W., Hendriks, D. F., & Scharpe, S. S. Carboxypeptidase U, a plasma carboxypeptidase with high affinity for plasminogen. *J. Biol. Chem.* 269, 15937-15944 (1994).
51. Deiteren, K. and Lambeir, A. M. A preliminary study of the stability, catalytic activity and Zn affinity of human carboxypeptidase M (CPM) and some of its glycosylation mutants. *FEBS J.* 272 [s1], [G2-032P]. 2005.
52. Hendriks, D., Scharpe, S., & van Sande, M. Assay of carboxypeptidase N activity in serum by liquid-chromatographic determination of hippuric acid. *Clin. Chem.* 31, 1936-1939 (1985).
53. Fekkes, D., van Dalen, A., Edelman, M., & Voskuilen, A. Validation of the determination of amino acids in plasma by high-performance liquid chromatography using automated pre-column derivatization with o-phthaldialdehyde. *J. Chromatogr. B Biomed. Appl.* 669, 177-186 (1995).
54. Weidinger, S. Reliable phenotyping of alpha-1-antitrypsin by hybrid isoelectric focusing in an ultranarrow immobilized pH gradient. *Electrophoresis* 13, 234-239 (1992).
55. Neuhoff, V., Arold, N., Taube, D., & Ehrhardt, W. Improved staining of proteins in polyacrylamide gels including isoelectric focusing gels with clear background at nanogram sensitivity using Coomassie Brilliant Blue G-250 and R-250. *Electrophoresis* 9, 255-262 (1988).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of making an alpha-1-proteinase inhibitor composition comprising des-lys aloha-1 proteinase inhibitor from human plasma, the method comprising the step of:
   treating a plasma precipitate comprising alpha-1-proteinase inhibitor with ethanol at a concentration of from 30% to 50%,
   wherein the plasma precipitate is selected from the group consisting of a Cohn fraction IV-1 precipitate and a Cohn fraction IV-1+IV-4 precipitate, and
   wherein the amount of des-lys alpha-1-proteinase inhibitor is increased.

2. The method of claim 1, wherein the amount of des-lys alpha-1-proteinase inhibitor in the composition treated with ethanol is more than 70% of total alpha-1-proteinase inhibitor in the composition.

3. The method of claim 1, wherein the amount of des-lys alpha-1-proteinase inhibitor in the composition treated with ethanol is more than 75% of total alpha-1-proteinase inhibitor in the composition.

4. The method of claim 1, comprising treating the Cohn fraction IV-1 or IV-1+IV-4 precipitate with ethanol at a final concentration of 50%.

5. The method of claim 1, comprising treating the Cohn fraction IV-1 or IV-1+IV-4 precipitate with ethanol at a final concentration of 40%.

6. The method of claim 1, comprising treating the Cohn fraction IV-1 or IV-1+IV-4 precipitate with ethanol at a final concentration of less than 45% but greater than 35%.

7. The method of claim 1, comprising treating the Cohn fraction IV-1 or IV-1+IV-4 precipitate at a pH greater than pH 5.9.

8. The method of claim 1, wherein the plasma precipitate is a Cohn fraction IV-1 precipitate.

9. The method of claim 1, wherein the plasma precipitate is a Cohn fraction IV-1+IV-4 precipitate.

10. An alpha-1-proteinase inhibitor composition comprising a physiologically acceptable carrier and an amount of des-lys alpha-1-proteinase inhibitor that is more than about 70% of total alpha-1-proteinase inhibitor in the composition, the composition made using the method of claim 1.

11. An alpha-1-proteinase inhibitor composition comprising a physiologically acceptable carrier and an amount of des-lys alpha-1-proteinase inhibitor that is more than about 75% of total alpha-1-proteinase inhibitor in the composition, the composition made using the method of claim 1.

* * * * *

UNITED STATES PATENT AND TRADEMARK OFFICE
CERTIFICATE OF CORRECTION

PATENT NO.         : 8,772,240 B2
APPLICATION NO.    : 11/749944
DATED              : July 8, 2014
INVENTOR(S)        : Peter Matthiessen et al.

Page 1 of 1

It is certified that error appears in the above-identified patent and that said Letters Patent is hereby corrected as shown below:

In the claims:

Claim 1, Col. 19, line 20, please delete "aloha" and insert --alpha--

Signed and Sealed this
Thirty-first Day of March, 2015

Michelle K. Lee
*Director of the United States Patent and Trademark Office*